US012678562B1

(12) United States Patent
Davie et al.

(10) Patent No.: US 12,678,562 B1
(45) Date of Patent: Jul. 14, 2026

(54) MODULATION OF VASCULAR ADAPTATION WITHIN A TUMOR TO INCREASE THERAPY UPTAKE WITHIN THE TUMOR

(71) Applicant: TriSalus Life Sciences, Inc., Westminster, CO (US)

(72) Inventors: Scott Davie, Boulder, CO (US); Trevor McCaw, Corte Madera, CA (US); Michael Brick Markham, Boulder, CO (US); David Benjamin Jaroch, Arvada, CO (US)

(73) Assignee: TriSalus Life Sciences, Inc., Westminster, CO (US)

( * ) Notice: Subject to any disclaimer, the term of this patent is extended or adjusted under 35 U.S.C. 154(b) by 1341 days.

(21) Appl. No.: 17/347,463

(22) Filed: Jun. 14, 2021

Related U.S. Application Data

(60) Provisional application No. 63/039,287, filed on Jun. 15, 2020.

(51) Int. Cl.
A61M 5/168 (2006.01)
A61M 5/142 (2006.01)
(52) U.S. Cl.
CPC ........ A61M 5/16859 (2013.01); A61M 5/142 (2013.01); A61M 5/1684 (2013.01); A61M 5/16881 (2013.01); A61M 2005/16868 (2013.01); A61M 2205/3331 (2013.01)
(58) Field of Classification Search
CPC .............. A61M 5/16859; A61M 5/142; A61M 5/1684; A61M 5/16881; A61M 2005/16868; A61M 2205/3331; A61M 5/16831; A61M 5/16836; A61M 5/16854; A61M 5/16877; A61M 2005/1726; A61M 2025/0002; A61M 2025/1052; A61M 2025/1095; A61B 17/1204; A61B 17/12109; A61B 17/12136; A61B 5/02007; A61B 5/021; A61B 5/0215; A61B 5/4839; A61B 5/6853
See application file for complete search history.

(56) References Cited

U.S. PATENT DOCUMENTS

| | | | |
|---|---|---|---|
| 8,696,698 B2 | 4/2014 | Chomas et al. | |
| 9,770,319 B2 | 9/2017 | Pinchuk et al. | |
| 2016/0310148 A1* | 10/2016 | Allen ............... | A61B 17/12136 |

(Continued)

*Primary Examiner* — Jason E Flick
(74) *Attorney, Agent, or Firm* — Wan Chieh Lee; Haug Partners LLP

(57) ABSTRACT

A method is provided to modulated vascular adaptation within a tumor so that therapy uptake is increased. The method includes providing a pressure directed therapy system having an infusion lumen, an occluder, a pressure sensor to sense pressure distal of the occluder. The distal end of the system is advanced to a target artery of an organ. The pressure in the target artery is reduced by expanding the occluder at the distal end of the system. Then, the therapy is infused through the infusion lumen and into the target artery. Upon sensing decreased pressure and thus vessel adaptation, infusion is stopped until vessel re-adaptation occurs. Then infusion resumes. The infusion continues in a cycle of therapy infusing, sensing pressure and determining vessel adaptation, waiting, and resuming once re-adaptation occurs until the therapy dose is delivered to the patient.

15 Claims, 7 Drawing Sheets

(56)     References Cited

U.S. PATENT DOCUMENTS

| 2017/0189654 A1 * | 7/2017 | Schwartz | ............ | A61M 5/1723 |
| 2018/0263752 A1 * | 9/2018 | Pinchuk | ................ | A61F 2/0108 |
| 2020/0383688 A1 | 12/2020 | Olson et al. | | |
| 2023/0355934 A1 * | 11/2023 | Agah | ................ | A61M 25/1002 |

* cited by examiner

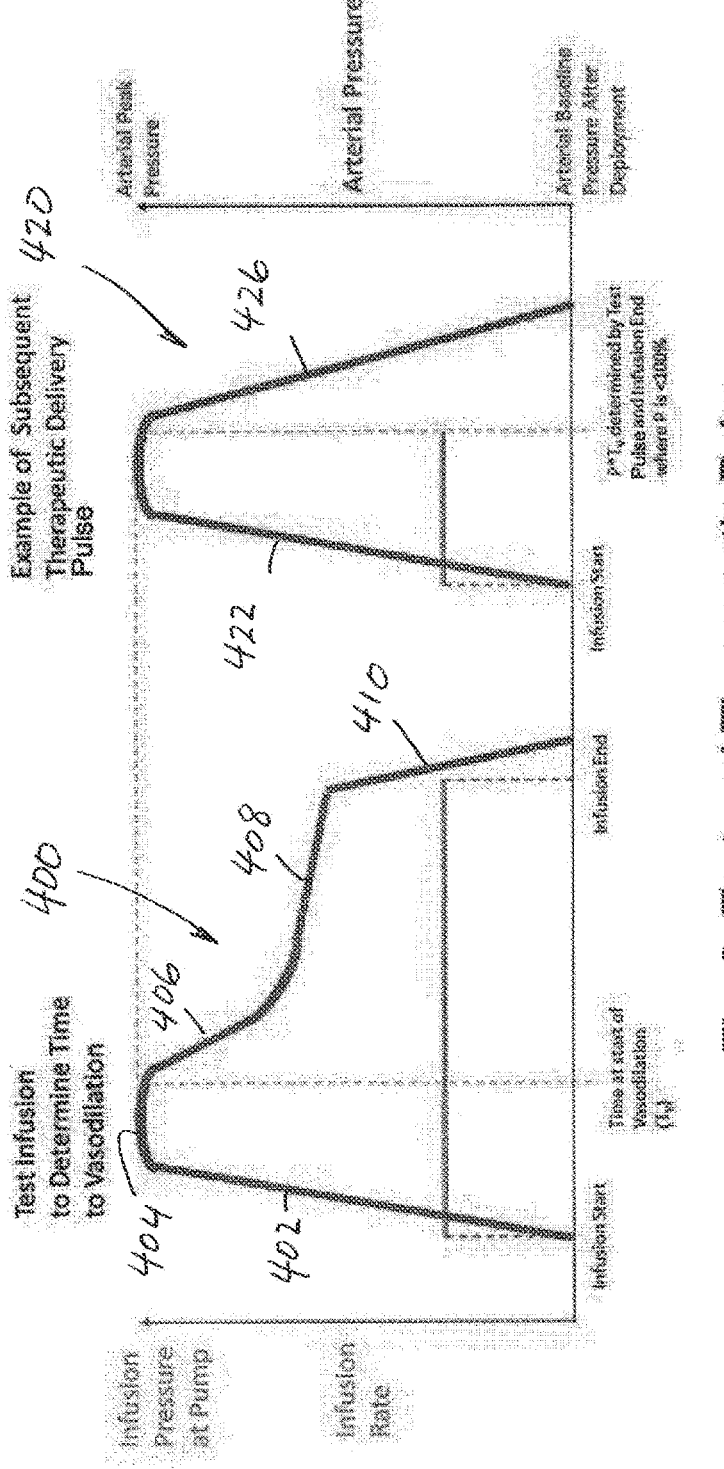
Fig. 8: Test and Therapeutic Pulses

MODULATION OF VASCULAR ADAPTATION WITHIN A TUMOR TO INCREASE THERAPY UPTAKE WITHIN THE TUMOR

CROSS-REFERENCE TO RELATED APPLICATION

The application claims benefit to U.S. Provisional Application Ser. No. 63/039,287, filed Jun. 15, 2020, which is hereby incorporated by reference herein in its entirety.

BACKGROUND OF THE INVENTION

1. Field of the Invention

The present invention relates to catheter-based therapeutic delivery methods for treatment of disease.

2. State of the Art

Healthy arterial blood vessels are surrounded by a layer of smooth muscle that acts to dilate or constrict the vessels based on a variety of physiological stimulus. One form of stimuli are shifts in blood pressure resulting from movement or exertion. Upon such stimuli, the body attempts to maintain a consistent pressure in the arterial vessel in order to maintain adequate blood flow to downstream tissues and achieve internal homeostasis.

In distinction, arterial blood vessels in cancerous tissues lack the ordered smooth muscle architecture of normal vascular tissues. As such, they are unable to adapt to changes in blood pressure or external stimulus. On the periphery of a large solid tumor, the aberrant physiology results in a zone of hypervascularization with large dilated arterial vessels. Blood pressure in such arterial vessels is often lower than in surrounding tissue. Further within the tumor, interstitial fluid pressure and solid tissue stress from the growing tumor cells act to compress the arterial vessel wall, resulting in narrow vessels highly resistant to fluid flow. The combination of a low pressure, hypervascular network immediately adjacent to flow resistant constricted arterial vessels results in minimal blood flow into the core of large solid tumors.

Standard delivery of therapeutics into large solid tumors includes supplying a series of hand-delivered, short, pulsatile quantities of the therapeutic through a catheter and into an artery feeding into the solid tumor. Such therapy will follow the path of least flow resistance. It is anticipated that some of the therapy will pass through the low pressure dilated vessels and exit the organ without targeting the flow resistant constricted arterial vessels in the core of the tumor. It is also anticipated that another portion of the therapy will be deposited in the vessels without penetrating the flow resistant arterial vessels. This results in limited partial treatment of the cancerous tissues.

SUMMARY

The autoregulatory system of normal vasculature is manipulated to preferentially direct therapy into vessels in diseased tissues, including tumors, using a pressure directed therapy system.

In an embodiment, the pressure directed therapy system includes a flexible tubular member having a proximal end, a distal end, and defining an infusing lumen extending between the proximal and distal ends, a diametrically adjustable vessel occluder mounted at the distal end, and at least one pressure sensor. The vessel occluder is preferably mechanically adjustable in diameter and includes a plurality of elastic filaments, the respective proximal and distal ends of which can be displaced relative to each other to expand and collapse the vessel occluder. In one embodiment, the flexible tubular member includes an inner catheter longitudinally displaceable relative to an outer catheter. The inner catheter defines the infusion lumen with a distal orifice and a flush lumen is defined at least in part by the outer catheter and preferably between the inner and outer catheters. The proximal ends of the filaments are coupled to the outer catheter and the distal ends of the filaments are coupled to the inner catheter. Longitudinal displacement of the inner and outer catheter relative to each other results in expansion of the occluder to extend across a wall of an artery feeding the diseased tissue. In an alternate embodiment, the vessel occluder is an inflatable balloon.

The tubular member, with occluder and pressure sensor, is advanced in a delivery configuration into the artery feeding the diseased tissue. Then the device is expanded relative to the delivery configuration to cause an initial drop in pressure distal to the occluder. The drop in pressure causes healthy vessels to constrict in an attempt to increase arterial pressure and return to homeostasis. Abnormal diseased vasculature, particular in a tumorous tissue, is unable to constrict in this manner. The result is that normal healthy tissues undergo constriction, while the diseased tissue vessels will remain open, low pressure vasculature. Blood and therapeutics will preferentially flow toward the low pressure diseased tissue under these conditions; however, only the peripheral hypervascular network of the diseased tissue will be accessible, as the circulating fluid will lack the pressure required to access the internal compressed vascular network.

Then, the use of cyclic infusion of therapy under pressure is employed to access resistive tumor tissues while maintaining enhanced specificity for the diseased tissue. Infusion of therapy at constant flow rate compensates for the loss of fluid pressure initially caused by the deployed occluder and can controllably exceed baseline pressure.

During the initial stages of therapy infusion, normal vasculature remains in the constricted state (caused by the initial decrease in pressure generated by the deployed occluder). These constricted vessels remain temporarily resistant to flow as the pressure generated by the system increases. For approximately 0.5 to 4 seconds, the diseased tissue with aberrant vasculature remains the path of least resistance to the flow of therapy delivered by the device. This therapy is delivered in a high-pressure state capable of overcoming internal tumor vessel restrictions.

As infusion of therapy progresses at a given fixed flow rate (until the desired volume of therapy is delivered), the pressure in the distal tissue compartment drops as healthy vessels adapt to increased pressure by dilating. This physiological change is monitored and detected by the pressure sensor. Once a drop in arterial pressure is detected during infusion, signaling physiological vessel adaptation, a feedback system is adapted to temporarily stop infusion. The pressure sensor detects the break in infusion with a pressure drop below that initially observed during infusion alone, as the dilated vessels will cause a transient decrease in overall pressure. The vessels then once again attempt to correct the pressure drop by constricting. This is detected by the pressure sensor as an increase and subsequent stabilization of distal or downstream pressure in the artery. Once pressure has stabilized to a set level, subsequent infusions of therapy can resume a cyclic form: infusion at a constant rate to generate at high downstream pressure until downstream pressure beings to decrease past a set pressure, stopping infusion, waiting and monitoring arterial pressure to identify that pressure has returned to a set pressure limit to determine that the vessels have re-constricted; i.e., re-adaptation. The subsequent infusions are stopped once the desired total volume of therapy has been delivered to the patient.

Then the occluder is collapsed into a smaller withdrawal configuration, and the pressure directed therapy system is for removed from the patient.

BRIEF DESCRIPTION OF THE DRAWINGS

FIG. 8 is a graph illustrating intravascular pressure changes over time during stages of the method of FIG. 7.

DETAILED DESCRIPTION OF THE PREFERRED EMBODIMENTS

Figure 1:
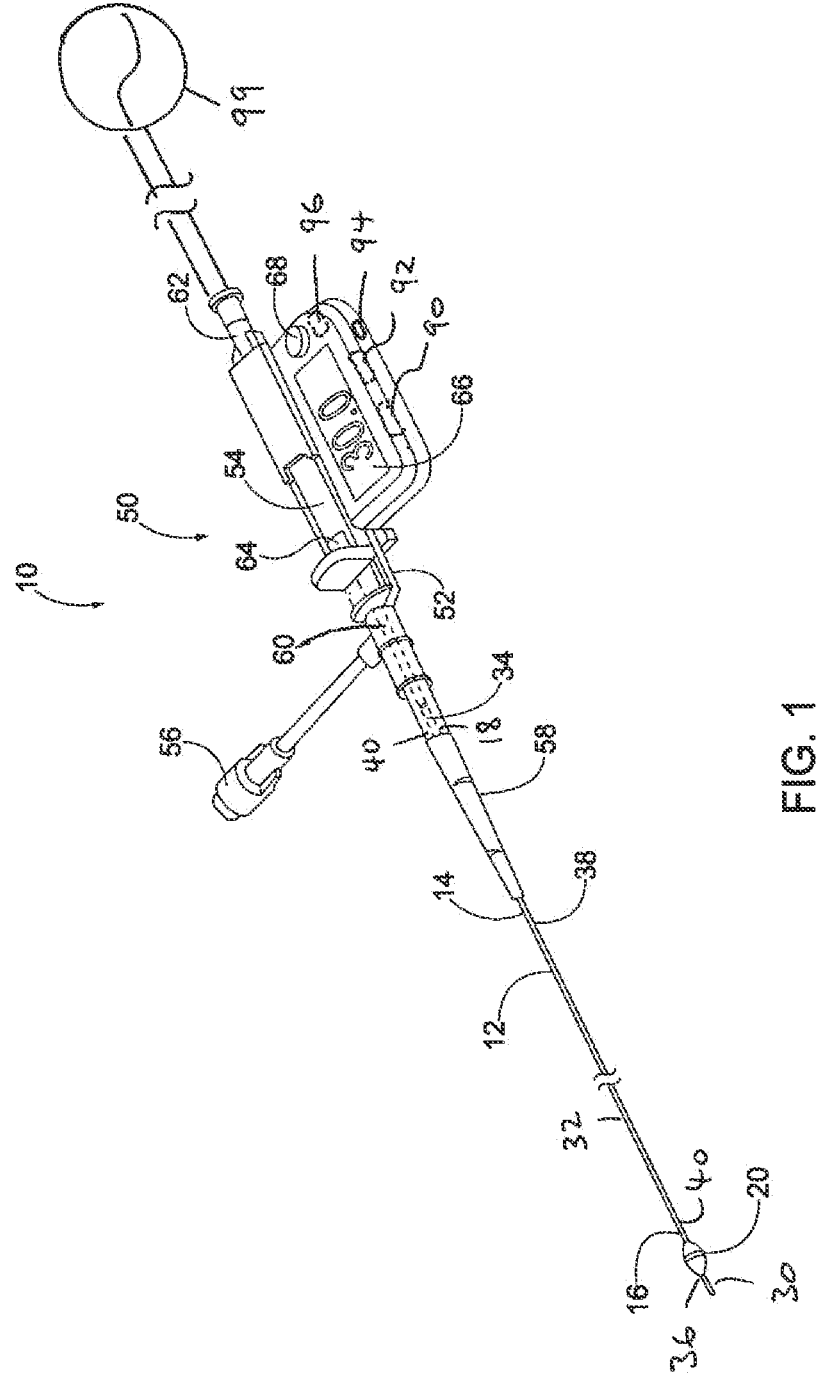
FIG. 1 is a perspective view of a pressure directed therapy system as described in an embodiment herein.

With reference to the following description, the terms "proximal" and "distal" are defined in reference to a user of the device, with the term "proximal" being closer to the user's hand, and the term "distal" being further from the user such as to be located further within a body of the patient during use.

Apparatus and methods are described herein related to the use of a system to inject a therapeutic agent into a primary arterial vessel communicating with a diseased tissue of an organ, for example, a tumor. For example, the tumor to be treated can be a solid tumor. In some cases, the tumor can be a cancerous tumor, such as a tumor specific to, by way of example only, cancer of the pancreas, kidney, liver, lung, or uterus. While the system and method are primarily referenced with respect to the treatment of solid tumors, it is also anticipated that other disease states of solid tissues may be treated, and the method is sufficiently broad to cover such other disease states of solid tissues.

As described herein, a treatment system is used to provide a therapy into a solid tumor by targeted infusion of the therapy into a region of tissue. The therapy is injected under relatively high pressure (compared to systemic pressure) into a region of an organ or other defined area of tissue served by one or more feeder arteries.

The therapy, i.e., therapeutic agents, referred to herein can be any agent which it is anticipated will have a therapeutic effect for treatment of the tumor in the patient. Many such potential therapeutic agents can be used, based on the type of cancer and the target organ to which treatment is directed. It is anticipated that the methods described herein can be practiced with all non-embolic therapeutic agents adapted to treat tumors. By way of example only, the therapeutic agents can be one or more immunotherapy agents, which can be used alone or in combination, including immunomodulators, vaccines, modified cells and check-point inhibitors. More particularly, immunomodulators can include IL-2, IL-7, IL-12, Interferons, G-CSF, Imiquimod, CCL3, CCL26, CXCL7, cytosine phosphate-guanosine, oligodeoxynucleotides, and glucans, which operate to increase the patient's immune response. Vaccines comprise an infusion of antigen directly or antigen-activated dendritic cells, which activate the patients white blood cells. Modified cells are blood-derived immune cells from the patient which are engineered and incubated to grow to a large number of modified cells that specifically target a region of tumor. This approach, referred to as adoptive cell transfer (ACT) has generated remarkable responses in the small clinical trials in which it has been investigated. Check-point inhibitors include anti-PD-1, which block the patient's natural suppression of T-cells, thereby effectively increasing the time and number of T-cells that can fight cancer. Further, contemplated therapeutic agents include immunotherapy and non-immunotherapy agents that are unknown at the time of filing this application, and such should be considered within the scope of the systems and methods described herein.

Figure 2:
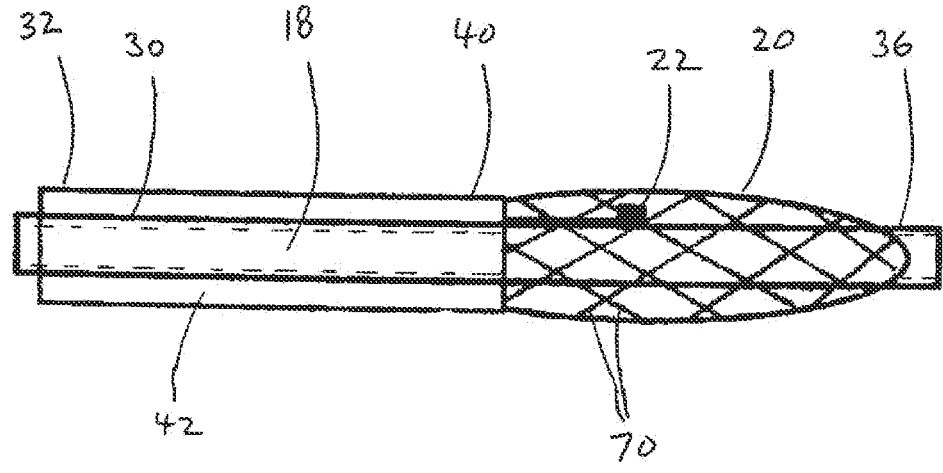
FIG. 2 is an enlarged schematic side elevation view of the distal side of the system of FIG. 1, shown with an occluder in a reduced diameter configuration for guidance to a target vessel.

Turning now to FIGS. 1 and 2, one pressure directed therapy system 10 is substantially as described in co-owned US Pub. No. 2020/0383688A1, which is hereby incorporated by reference herein in its entirety. Such a system 10 includes a flexible tubular member 12 having a proximal end 14 a distal end 16. The tubular member 12 defines an infusing lumen 18 extending between its proximal and distal ends. A diametrically adjustable vessel occluder 20 is mounted at the distal end 16 of the tubular member. The system also includes at least one pressure sensor 22 located and functioning as described below.

In an embodiment, the flexible tubular member 12 includes an inner catheter 30 telescopically advanceable within an outer catheter 32. The inner catheter 30 has a proximal end 34 and distal end 36, and the outer catheter 32 also has a proximal end 38 and distal end 40. The infusion lumen 18 is preferably defined through the inner catheter 30 and opens to a distal axial orifice 84, and a separate flush lumen 42 is preferably defined in the toroidal space between the inner and outer catheters. Alternatively, the flush lumen may extend through the wall of either of the inner and outer catheters 30, 32.

An actuation handle 50 is provided at the proximal ends 34, 38 of the inner and outer catheters 30, 32 to effect relative displacement of the thereof. The actuation handle 50 includes a stationary member 52 and a movable member 54, such as a slide longitudinally displaceable relative to the stationary member. The stationary member 52 is provided with a side port 56, and a strain relief 58 connects the proximal end 38 of the outer catheter 32 to the stationary member 52. The side port 56 is in fluid communication with the outer catheter 32. The movable slide 54 is coupled to the inner catheter 30. A hypotube 60 is coaxially inserted around the proximal end of the inner catheter 34 to provide mechanical support of the inner catheter. The proximal end of the slide 54 defines an infusion port 62 that is fluidly coupled to the proximal end 34 of the inner catheter 30. The actuation handle 50 also includes a releasable lock 64 that, when actuated, can retain the movable member 54 and stationary member 52 in relatively fixed longitudinal positions. The handle 50 may also include an integrated or associated memory 90 for storage of data related to sensed pressures and a programmed logic chip 92 to perform functions on the stored pressure data. The handle may also include an integrated or associated display 66 to display the stored data or results of the logic functions. Button 68 near display permits actuation of the logic and display as well as cycling through various logic functions. The handle may also include a communications port 94 to permit the system 10 to communicate with off-handle memory, logic, displays, the infusion pump, and other peripheral devices and accessories. As an alternative or addition to communications port 94, the handle may include a wireless transmitter/receiver 96 for such communications with peripheral devices and accessories.

Figure 3:
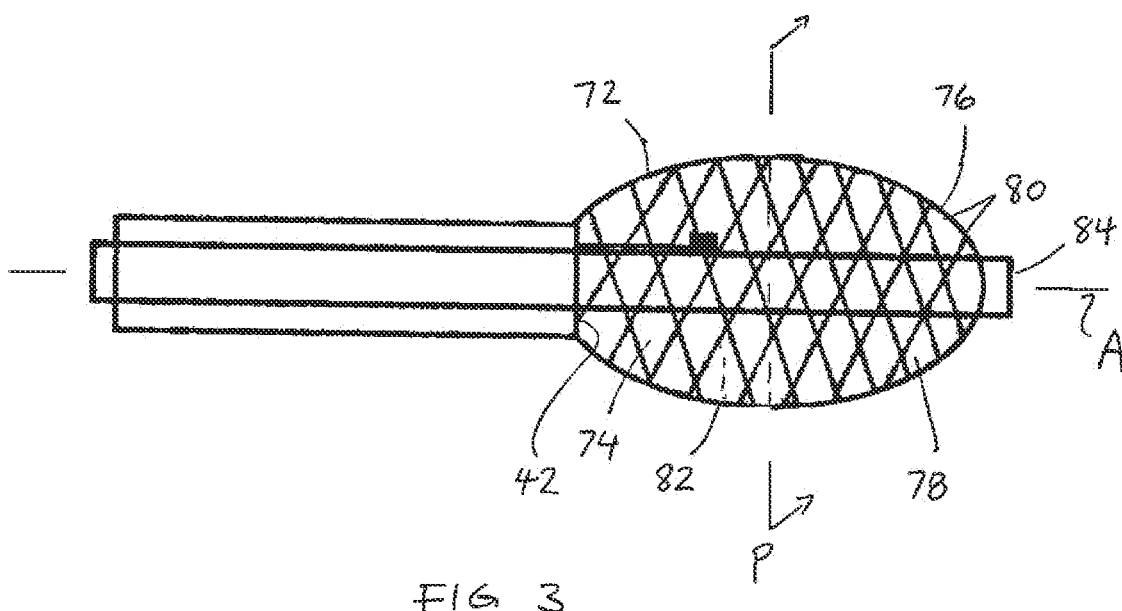
FIG. 3 is a view similar to FIG. 2, shown with the occluder in an enlarged diameter configuration for occlusion of the target vessel.

In an embodiment, the occluder 20 is a microvalve comprising a braided construct of filaments 70. The proximal end of the filaments 70 are coupled to, and preferably rigidly fixed to, the distal end 40 of the outer catheter 32, and the distal end of the filaments 70 are coupled to, and preferably rigidly fixed to, the distal end 36 of the inner catheter 30. The general construct of the braided valve portion of such a microvalve device is described in detail in co-owned U.S. Pat. Nos. 8,696,698 and 9,770,319, both of which are hereby incorporated by reference herein in their entireties. Longitudinal displacement of the inner catheter 30 relative to the outer catheter 32 results in the microvalve moving between a first elongate ovoid configuration of smaller diameter (FIG. 2) adapted for guiding to a deployment location in a vessel, and a second squatter ovoid configuration of a larger diameter adapted for occlusion of the vessel (as shown in FIG. 3). That is, in both the first and second configurations, the microvalve is of an ovoid configuration and has a generally symmetrically shape about a longitudinal central axis A and a plane P orthogonal to the central axis A of the microvalve at its area of maximum diameter. It is recognized that the occluder can be moved through the first and second configurations, and any size of configuration therebetween to best suit the vessel in which it is used. The lock 64 on the handle 50 can facilitate retaining the occluder 20 in a desired size configuration during therapeutic treatment. The system 10 can be advanced in the first elongate configuration to a deployment location in a blood vessel over a guidewire (not shown) inserted through the infusion lumen 18 of the inner catheter 30. The interior of the occluder 20 defines a chamber 82.

In accord with one aspect of the occluder 20, a fluid impermeable membrane 72 is provided over the proximal portion 74 of the braided construct. Suitable materials for the impermeable membrane include elastomeric natural and artificial rubbers, silicones, styrenics, olefinics, copolyesters, polyurethanes and polyamides. In accord with another aspect of the occluder, a fluid permeable coating or covering 76 is provided over a distal portion 78 of the braided construct. Suitable materials for the fluid permeable coating 76 include elastomeric natural and artificial rubbers, silicones, styrenics, olefinics, copolyesters, polyurethanes and polyamides processed so as to have micro or macro scale perforations, channels, pores, or fibrous rather than continuous morphology. This may be accomplished by physical perforation techniques, by electrospinning or melt spinning fibers, by inclusion of soluble components that can be removed during processing to leave pores or voids, and by the addition of open pore foaming agents or other suitable technology. The coating or covering 76 can include a material placed over the outer surface of the filaments 70, within the inner surface of the filaments, or a combination thereof. The coating or covering 76 can extend only between the filaments. The coating or covering 76 can be freefloating on the filaments or can be rigidly fixed to the filaments. The coating or covering 76 can be applied by dip coating, spraying, sewing, bonded application, or other suitable technology. The fluid permeable material 76 can be an otherwise impermeable material made permeable by perforations or apertures 80.

As the flush lumen between the inner catheter and outer catheter is in fluid communication with the proximal infusion port, a pressure sensor may reside within this space and still monitor pressure experienced at the distal tip as long as the proximal infusion port is sealed (creating a closed pressure chamber in communication with the distal tip of the catheter).

The pressure sensor 22 may be mounted within the chamber 82 to shield the sensor from noise generated by turbulent flow as therapy exits the distal tip of the system. The pressure sensor 22 also may be mounted on the distal exterior of the occluder. The pressure sensor 22 also be mounted on the inner catheter distal of the occluder. The pressure sensor can also be mounted proximally on the system, for example, at the side port 56 of the handle or in the infusion port 62 of the handle. The pressure sensor 22 can be mounted in any location or manner that permits it to accurately and responsively obtain pressure readings from downstream locations within the target artery.

The system is preferably used in combination with an infusion pump 98 coupled to the infusion port 62. The infusion pump 98 is configured to infuse a therapy at a variable or a constant rate, in discrete portions of a total prescribed dose as described further below. The infusion pump 98 is in communication with the logic chip 92 such that when the logic determines, based on calculations on the stored pressure data, that predetermined conditions exists within the target artery, the logic can interrupt the infusion pump; and when the logic chip 92 determines that other predetermined conditions exists within the target artery, the logic chip can initiate resumption of infusion of the therapy.

Figure 4:
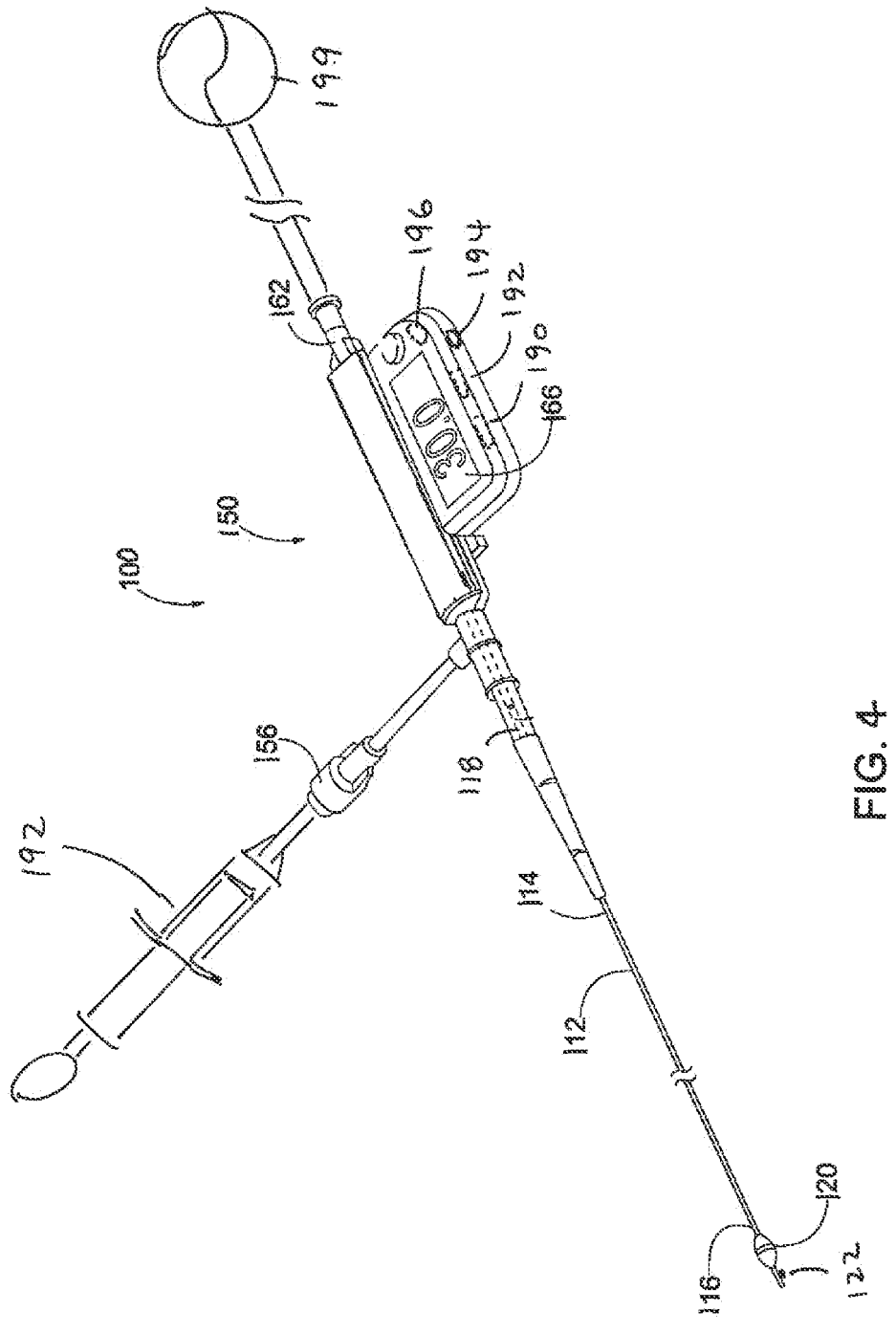
FIG. 4 is one alternative embodiment of a pressure directed therapy system.

Turning now to FIG. 4, another embodiment of a pressure directed therapy system 110, substantially similar to the system 10 described above (with like parts having reference numerals incremented by 100), is shown. The system 110 includes a flexible tubular member 112 having a proximal end 114 a distal end 116. The tubular member 112 defines an infusing lumen 118 extending between its proximal and distal ends. A diametrically adjustable vessel occluder 120 in the form of an inflatable member is mounted at the distal end 116 of the tubular member. The system also includes a pressure sensor 122 located for sensing fluid pressure on the tubular member 112 at distal side of the inflatable member 120. The inflatable member 120 is sized to be diametrically expanded into contact with the vessel wall by injection of an inflation fluid into the inflatable member to thereby create a fluid barrier within the vessel in which it is to be deployed. A handle 150 is provided with a port 156 for injection of the inflation fluid, e.g. via a lockable syringe 199, and an infusion port 162 for infusion of the therapy through an infusion pump 198 in communication with the system 10. The handle 150 also includes a display 166 for display of critical (and optionally non-critical) data, a memory 190, a logic chip 192, and/or communication ports 194 and/or transmitter/receivers 196 for communication with such elements, as discussed above with respect to system 10.

Other pressure directed therapy systems having an occluder of a different construct from that previously described can similarly be used in the methods described herein. For purposes of clarity and simplicity, the following methods will be described with respect to the system 10

(with all reference numerals between 10 and 99 referring to the system shown in FIGS. 1 to 3); however, a like procedure can be carried out with any suitable alternative pressured directed therapy system, such as embodiment 110 and the method is equally applicable and covers all such suitable alternatives without requiring further description for one skilled in the art to practice such method.

Figure 5:
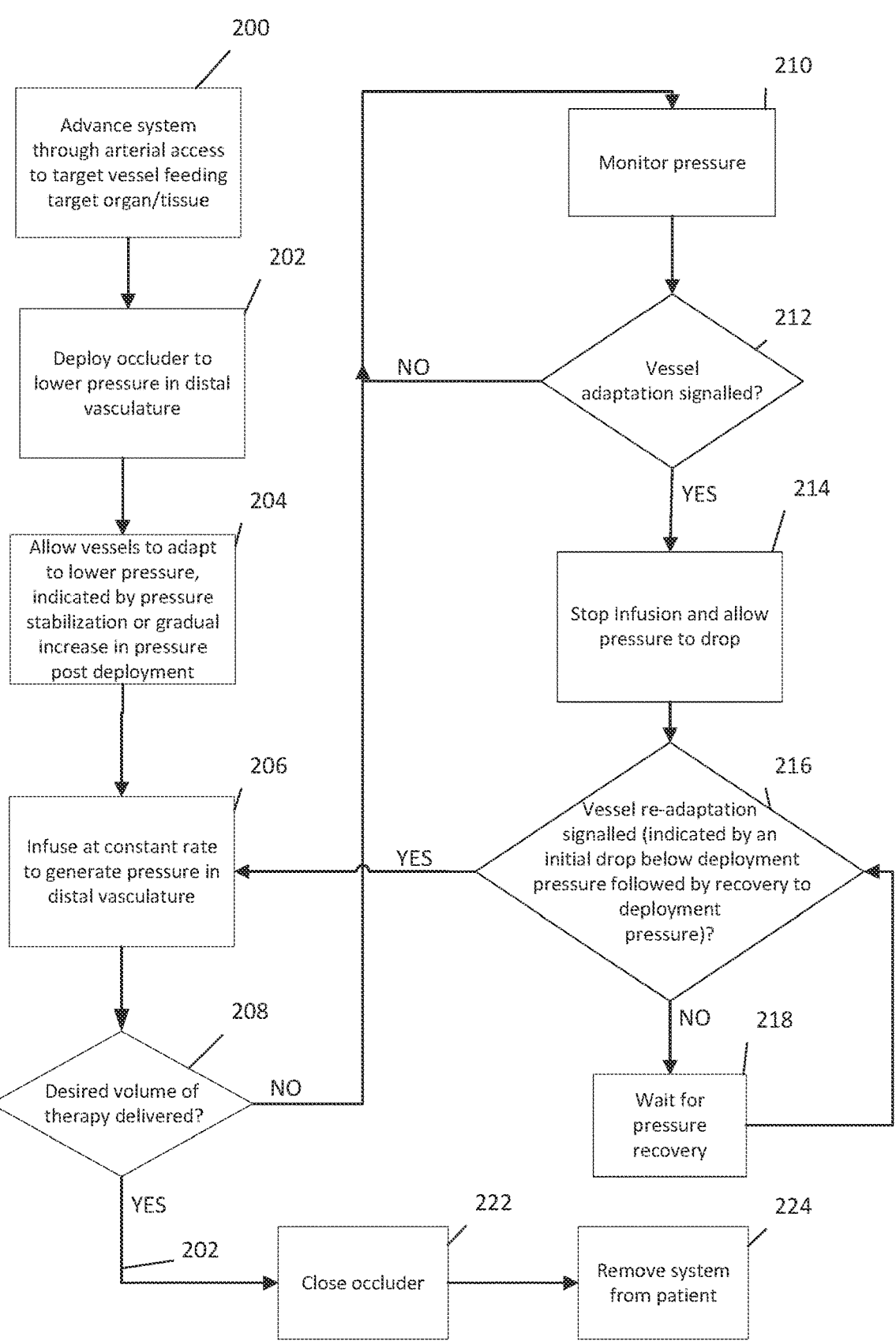
FIG. 5 is a flow chart of a method of using the systems described herein for modulation of vascular adaptation.
Figure 6:
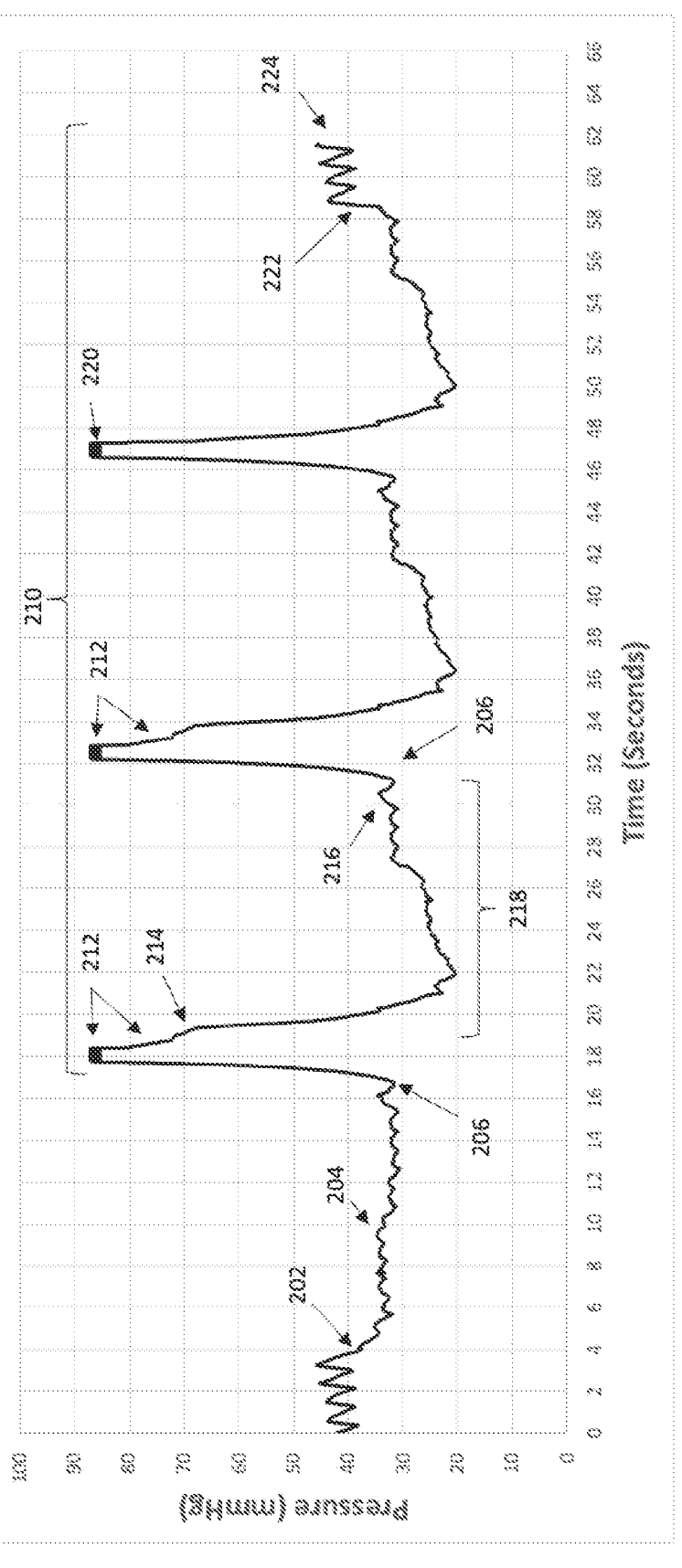
FIG. 6 is a graph illustrating in vivo human study intravascular pressure changes over time during indicated stages of the method, and particularly illustrating vascular adaptation and re-adaptation.

Turning now to FIGS. 5 and 6, in accord with a method of using the system, the distal end of the system 10 is advanced at 200 in the reduced diameter configuration to a target vessel of an organ in accord with known procedures. In that manner, the system 10 can be tracked over a guidewire through the arterial system to an intended location adjacent or within the target organ. The target vessel is preferably an artery delivering a supply of blood from to an organ. By way of examples only, the organ can be the liver and the target artery can be the right hepatic artery, left hepatic artery, common hepatic artery or any branches thereof; the organ can be pancreas and the target artery can be gastroduodenal and splenic artery and branches thereof; the organ can be the kidney and the target artery can be the renal artery and branches thereof; the organ can be the spleen and the target artery can be the splenic artery; the organ can be the prostate and the target artery can be the prostatic artery; the organ can be the uterus or tissue of uterine fibroids, and the target artery can be the uterine artery and associated branches. Other organs can be similarly treated through associated target vessels, preferably wherein the target vessel is an artery.

Once the distal end of the system is located within the within the target vessel, the pressure within the target vessel is measured over time with the pressure sensor 22 to obtain a running average baseline pressure for a period of time. All pressures sensed by the pressure sensor are preferably indicated on the handle display 66, but may also be indicated on an associated monitor (not shown), via wired communication at port 94 or wireless communication.

The handle 50 is then actuated to move the inner catheter 30 relative to the outer catheter 32 and expand the diameter of the occluder 20 at 202 to at least partially occlude the target artery and reduce flow therethrough. This results in lowering fluid pressure within the target artery. The pressure sensor 22 continuously senses the pressure at regular intervals, e.g., 10 times/sec and records the sensed pressure data in the memory 90. The logic chip 92 performs functions with respect to the pressure data stored in the memory 90, including maintain calculations of average running arterial pressure, peak average arterial pressure, and optionally a slope for the average arterial pressure over time, which are updated throughout the therapy procedure.

The handle lock 64 can be operated to fix the configuration (size and shape) of the occluder 20 within the vessel. It is not necessary that the occluder fully occlude flow within the artery, however that may be an optimum occlusive configuration for a particular artery and target organ. It is also appreciated that the design of the preferred occluder is intended to allow at least partial antegrade flow about the occluder even when expanded to the vessel wall. The average running pressure is monitored by the pressure sensor 22 (with functions performed in combination with memory 90 and logic chip 92), to identify homeostasis at 204, which is generally indicated by stabilization, which may be exhibited as a slight decrease in pressure relative to baseline pressure. Homeostasis indicates that the vessels have adapted to the lower pressure condition.

In addition, prior to infusion, the healthy vessels additionally may be primed to better divert infusion of the therapy to the vessels within the diseased tissue. Normally, the healthy vessels will constrict only a small amount when the occluder is opened within the vessel. However, the size of the occluder within the vessel and the potential force the occluder exerts against the vessel wall can effect a reduced flow through the vessel, and consequent homeostasis condition with lower pressure conditions.

Once homeostasis is reached, therapy is infused at 206 by the infusion pump 98 at a preferably constant rate through the infusion port 62, into the infusion lumen 42, and out of the distal orifice 84.

Optionally, for a first infusion in the treatment, the system initially performs an internal pressure calibration to determine the infusion rate. A user inputs a desired pressure increase relative to baseline pressure (or homeostasis pressure). The system acquires the pre-deployment baseline pressure and then titrates the infusion rate of the therapy to achieve the intended increase in pressure above the baseline. The determined infusion rate is recorded at the infusion pump 98 (or elsewhere in the system) and preferably used as a constant rate for infusion for all subsequent therapy infusion.

The rate of infusion of therapy, which is relatively high compared to the normal rate of blood flow through the distal vasculature and subject to a high arterial pressure, compensates for the prior loss of fluid pressure initially caused by the expansion of the occluder within the vessel and controllably exceeds baseline pressure. Also, by way of example, the constant rate may be 1 to 5 cc/second. By way of example, where the running average of arterial pressure at baseline is 43 mmHg, and the running average arterial pressure during homeostasis is 32 mmHg, the running average of arterial pressure during infusion is 78 mmHg. That is, the running average homeostasis pressure is generally a 20 to 70 percent decrease relative to the running average baseline pressure in the target vasculature upon occluder deployment, and preferably is reduced by at least a 20 percent relative to the running average baseline pressure in the target vasculature upon occluder deployment, more preferably reduced by at least a 40 percent decrease relative to the running average baseline pressure in the target vasculature upon occluder deployment, and may even be reduced by at least a 50 percent, or even up to a 70 percent, decrease relative to the running average baseline pressure in the target vasculature upon occluder deployment. (The impermeable membrane covered occluder 20 described above and utilized in carrying out this method has been shown to have the ability to controllably, reliably, and repeatedly effect a running average homeostasis pressure decrease that is 0 percent and 90 percent of baseline pressure, and any suitable pressure decrease in that range can be appropriately utilized.) It is anticipated, though not conclusively determined at this point, that reducing pressure in the artery prior to infusion with the therapy may have criticality in diverting the infusion of the therapy to the vessels within the diseased tissue, as described above, and such reduction in pressure should preferably be of a degree to return such results. The running average pressure at infusion is generally 110 to 300 percent of running average baseline pressure in the target vasculature, and more preferably exceeds 180 percent of the running average baseline pressure; and exceeds 200 percent of the running average pressure at homeostasis, and is shown to exceed 240 percent of the running average pressure at homeostasis. It is possible that the pressure at infusion will be 250 percent or higher relative to the running average pressure at homeostasis.

During the initial stages of the infusion, normal vasculature remains in the homeostatic constricted state, caused by the initial decrease in pressure. The constricted vessels remain temporarily resistant to flow as the pressure generated by infusion from the system increases. For approximately 0.5 to 4 seconds, the tumor remains the path of least resistance to the flow of the therapy delivered by the device. The therapy is delivered in a sufficiently high pressure state capable of overcoming internal tumor vessel restrictions.

Infusion is constantly monitored at 208 at the pump 90 to determine whether a full dose of the therapy has been delivered, and the pressure at the target artery is continuously monitored at 210 to assess whether the vessel is subject to adaptation. Provided the full dose is not yet delivered and the vessel is not subject to adaptation, the infusion continues at a given fixed flow rate.

Vessel adaptation results when the healthy tissue downstream of the occluder and in the target organ adapts to the increased pressure of the constant rate high pressure therapy by dilating, resulting in lower pressure.

Vessel adaptation can be confirmed in several ways. In all preferred methods, vessel adaptation is sensed by the pressure sensor as a pressure drop occurring after the pressure rise resulting from the constant rate, high pressure infusion. In one method, vessel adaptation is confirmed by recording at least a 3 percent drop in the running average of pressure from the peak pressure; or at least a 5 percent drop in the running average of pressure from peak pressure; or at least a 10 percent drop in the running average of pressure from the peak pressure; or at least a 15 percent drop in the running average of pressure from the peak pressure.

Another method includes calculating the slope of a line best fitting the running average of the arterial pressure over time (or the slope of a tangent to a curve best fitting arterial pressure over time). No vessel adaptation is seen when the slope is positive or zero; vessel adaptation is confirmed when the slope becomes negative. To prevent noise in the sensing system or from systemic activity (such as heartbeats) from causing improper termination due to false confirmations of vessel adaptation, confirmation of the negative slope over a set period of time (by way of example only, 0.1 seconds, 0.2 seconds, or 0.4 seconds) may be required for confirmation.

Another method includes identifying a change in slope of the running average of the arterial pressure over time, as indicated above, and waiting a set time prior to signaling confirmation of vessel adaptation after the change in slope is identified. The delay is provided because even after the running average arterial vessel pressure begins to drop relative to peak pressure, there is short window in which the arterial vessels remain sufficiently open to optimally receive the therapy. The window may be 0.2-2 seconds. After the delay, vessel adaptation is confirmed.

According to another system and method, the system is coupled with sufficient logic to perform artificial intelligence functions to determine when vessel adaptation has occurred. For example, the system may be coupled via communications port 94 or transmitter/receiver 96 to an outboard logic system that is adapted to perform fuzzy logic to quickly identify the changes in running average pressure or other conditions that can be sensed and which indicate vessel adaptation. Upon sensing vessel adaptation, vessel adaptation is confirmed.

Once vessel adaptation is identified at 212, then the system circuit is programmed to temporarily stop the infusion at 214 by the infusion pump 98. Once the high pressure infusion therapy is stopped at 214, a further transient decrease in overall pressure will occur, as the vessels are dilated and no therapy is being infused. This transient decrease will be detected by the pressure sensor. The vessels will attempt to correct the pressure drop by constricting into a state of re-adaptation. The pressure sensor continuously monitors until this subsequent increase and stabilization of pressure in the artery distal of the occluder is detected. It is preferred that stabilization is indicated for at least 1 to 5 seconds and preferably at least 3 seconds.

When re-adaptation is identified at 216, infusion at a constant rate is resumed at 206 as previously performed until vessel adaptation is again identified at 212. Then, the infusion is again interrupted at 214 to wait at 218 for vessel re-adaptation at 216. The infusion is then continued in a series of like cycles of infusion, identified vessel adaptation, periods of sensing and monitoring for vessel re-adaptation prior to resuming continued therapy infusion until the full dose of the therapy is delivered to the patient at 220.

Once the full dose of therapy has been delivered, the pump stops delivering the therapy, the occluder is closed at 222 and the pressure directed therapy system is removed from the patient at 224.

Figure 7:
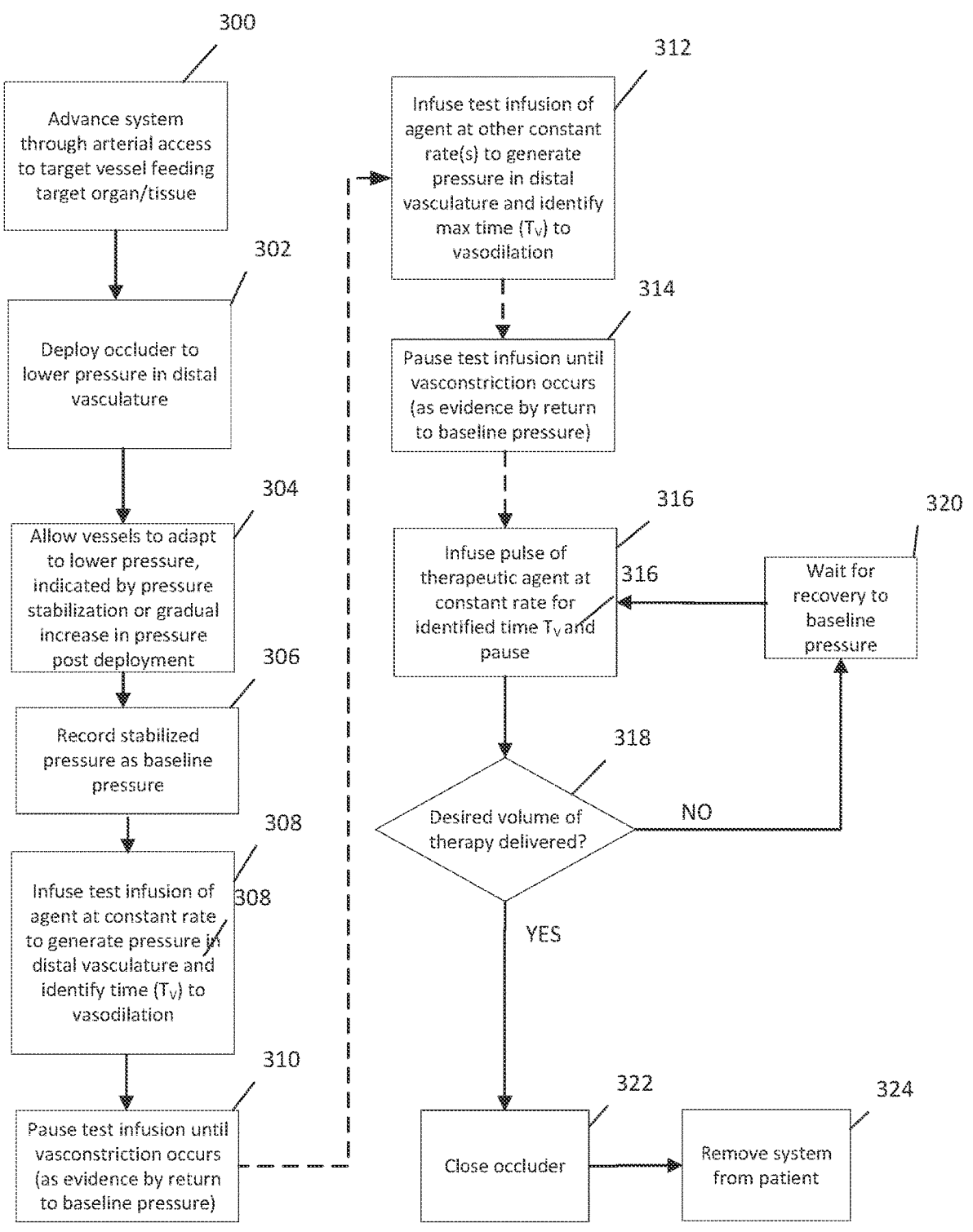
FIG. 7 is a flow chart of another method of using a pressure directed therapy system for modulation of vascular adaptation.

Turning now to FIGS. 7 and 8, another method of modulating vascular adaptation to increase uptake of a therapeutic is shown. An aspect of the method is that therapeutic delivery can be performed without continuous monitoring of pressure within the vessel. That said, as described below, various aspects of the method can be modified and/or optimized in combination with continuous pressure monitoring, as will be described. Steps of the method described with respect to FIGS. 7 and 8 are substantially the same as described with respect to the method of FIGS. 5 and 6, unless specifically distinguished as follows. The distal end of the system 10 is advanced at 300 in the reduced diameter configuration to a target vessel of an organ in accord with known procedures. The target vessel is preferably an artery delivering a supply of blood to an organ.

Once the distal end of the system is located within the target vessel, the occluder is deployed at 302. Deploying, i.e., expanding or otherwise operating the occluder to limit or prevent blood flow within the artery, lowers the pressure in the distal vasculature. After deployment, the vessels are provided time to adapt to the lower pressure at 304 which consequently results in vasoconstriction. Upon vasoconstriction, the pressure in the vessels stabilizes (or potentially gradually increases). The stabilized pressure is recorded at 306 as a baseline pressure. Alternatively, the baseline pressure can be calculated based on multiple intravascular pressure measurements over time and averaged.

Then, according to an aspect of the method in FIG. 7, a test pulse (i.e., a limited infusion) of a liquid agent is injected at 308 into the distal vasculature at a constant rate to generate pressure. The agent of the test pulse is preferably a non-therapeutic agent, such as saline, but optionally can be a first portion of the intended therapeutic agent or another agent having therapeutic properties. The test pulse 400 is delivered continuously for a period of time. The pressure is monitored in the vessel during the delivery of the test pulse to identify when vasodilation begins to occur in the target vessels. Referring to FIG. 8, during an initial portion 402 of the test infusion, the pressure increases as the vessels have previously constricted but are now subjected to a constant rate of infusion. During a second portion 404 of the test infusion, the pressure remains elevated and constant by the constant rate infusion. During a third portion 406 of the test infusion, the target vessels begin to adjust to the constant rate infusion by dilating, resulting in a first pressure drop in the vessels. The pressure drop can be determined by comparison of the absolute pressure to a percentage threshold or the slope of the calculated (rate of change in pressure over time) and identified to be negative or identified to be at a particular slope. During a fourth portion 408 of the test infusion 408, as delivery is continued after vasodilation begins to occur, the pressure in the vessels continues to decrease as the vessels further adjust to the constant rate flow and further dilate. Then, after the test infusion is stopped, the pressure further decreases while the vessels undergo recovery. An important aspect of the data is the time span from starting the first portion 402 of the test infusion to ending the second portion 404. That is, identifying the time Tv from initiating delivery until vasodilation begins to occur. The time Tv characteristic of the vasculature is used to optimize delivery and consequent uptake of subsequent delivered therapeutic, as discussed below.

Now, referring back to FIG. 7, after vasodilation occurs from delivery of the test infusion at 308, all infusion is paused at 310 until vasoconstriction re-occurs. The vasoconstriction is confirmed by measuring a return to baseline pressure in the target vasculature.

Optionally, one or more additional test pulses of an agent are delivered at 312 at different constant rates and the time to vasodilation Tv under each rate of the respective test pulses is recorded. Each test infusion is separated by a sufficient pause at 314 in infusion to allow the vessels to again constrict and resume baseline pressure conditions. From the one or several test pulses, the constant rate of infusion is selected such that the time Tv permits delivery of the maximum volume of therapeutic agent under the optimum conditions for uptake.

Then, a first pulse of the therapeutic agent is infused 316 through the system under the selected constant rate conditions for a time Tv and then paused. Referring to FIG. 8, the pulse 420 of therapeutic agent is delivered only during the portion of the infusion shown at 422 in which the vessels are in a constricted stated. As an option, the pulse of therapeutic can be delivered for a time that is shorter than time Tv, but preferably should not be delivered for a time longer than time Tv, as after time Tv the vessels will begin to dilate. After the first pulse the full dose of the therapy will only be partially delivered. As such, delivery of the therapy is paused at 320 until the vessels recover at 426 by undergoing vasoconstriction as indicated by a return to baseline pressure. Then, subsequent pulses of therapy are delivered in a like manner (at pulses of time Tv) and then paused to permit recovery to baseline pressure (+10%). An advantage of the procedure is that it is known that therapy will be delivered only when the vessels are constricted, so that the therapy is infused under conditions compatible with therapeutic uptake. Furthermore, such optimum conditions for delivery and uptake can be determined with the test infusion and then thereafter used to carry out the infusion of the therapy without further pressure monitoring.

After the dose of the therapy is delivered, the occluder is closed at 322, and the delivery system is removed from the patient at 324.

Several optional variations to the above method can be implemented. While it is not necessary to monitor intravascular pressure after the test pulse, the pressure may nevertheless be monitored throughout the procedure. Then, for example, if the intravascular pressure during infusion indicates that vasodilation is occurring at an earlier time than expected, that is before time Tv, then this new earlier time can be set as an updated time Tv for future pulses to ensure that the maximum therapeutic is delivered under vasoconstricted conditions such updates can be further made on an as needed basis. In addition, the occluder can be configured to temporarily slow or stop the blood flow within the arterial vessel after each pulse of the therapeutic agent is delivered. This slowing or stopping of the flow increases the dwell time of the therapeutic agent within the target tissue and consequently increases therapeutic uptake. According to another optional variation, with the occluder deployed in the open configuration, each pulse can be timed to be delivered during systole, which would provide increased flow through the target tissue during infusion or prevent flow during periods of non-infusion. The optional variations may be utilize individually or in combination.

There have been described and illustrated herein embodiments of systems and methods for intravascular delivery of a therapeutic agent through a vessel to a tissue, such as an organ. While particular embodiments of the invention have been described, it is not intended that the invention be limited thereto, as it is intended that the invention be as broad in scope as the art will allow and that the specification be read likewise. Thus, it is recognized that the systems and methods may be applied to both humans and animals. Also, while examples of organs and disease states have been provided, such lists are not meant to be exclusive and the systems and methods are intended to be used where ever they would have therapeutic utility, in association with any such organs, disease states, and with any appropriate therapeutic agents now known or hereinafter discovered or developed. Also, the flexible tubular member can be any catheter arrangement meeting the needs of the device claimed, i.e., permitting passage of the therapeutic agent and actuation of the occluder. Further, while preferred occluders have been described, other occluders may be used as well to assemble the systems and accomplish the methods described herein. Also, while running average pressures are described for use in the method, it is recognized that other methods of acquiring pressure measurements including discrete measurements or other methods can be used as well. It will therefore be appreciated by those skilled in the art that yet other modifications could be made to the provided invention without deviating from its scope as claimed.

What is claimed is:

1. A method of delivering a dose of a therapy to an organ of a patient, comprising:
a) providing a pressure directed therapy system for delivering the therapy to a target artery feeding the organ of the patient, the system comprising,
i) a flexible tubular member having a proximal end and a distal end, an infusion lumen extending between the proximal and distal ends, the infusion lumen having a distal orifice at the distal end, wherein the flexible tubular member is configured to infuse the therapy into the target artery through the distal orifice;
ii) a deployable occluder mounted at the distal end of the tubular member, the occluder having a radially-collapsed, non-deployed configuration and a radially-expanded, deployed configuration; and
iii) a pressure sensor configured to sense fluid pressure in the target artery distal of the occluder;
b) advancing the occluder in the non-deployed configuration to the target artery of the organ;
c) sensing a first pressure in the target artery with the pressure sensor;
d) deploying the occluder into the deployed configuration within the target artery;

e) then infusing the therapy through the infusion lumen and out of the distal orifice at an infusion pressure higher than the first pressure, f) tracking a running peak infusion pressure;

g) upon sensing, with the pressure sensor, a predetermined decrease in the infusion pressure relative to the running peak pressure, stopping infusion;

h) waiting for the pressure in the target artery to return to within ±10% of the first pressure; and i) repeating steps e) through h) until the dose of the therapy has been delivered to the patient.

2. The method of claim 1, wherein the occluder of the system is a manually actuatable microvalve.

3. The method of claim 1, wherein the occluder of the system is an inflatable balloon.

4. The method of claim 1, wherein the infusing the therapy is at a constant rate.

5. The method of claim 1, wherein the sensing of the first pressure includes, sensing a baseline pressure in the target artery when the occluder is in the non-deployed configuration; and sensing a stabilized pressure in the target artery when the occluder is in the deployed configuration.

6. The method of claim 1, wherein deploying the occluder within the target artery at least partially reduces the fluid pressure within the target artery distal of the occluder.

7. The method of claim 1, wherein the predetermined decrease in infusion pressure is a decrease of at least 10% in the infusion pressure.

8. A method of delivering a dose of a therapy to an organ of a patient, comprising:

a) providing a pressure directed therapy system for delivering the therapy to a target artery feeding the organ of the patient, the system comprising, i) a flexible tubular member having a proximal end and a distal end, an infusion lumen extending between the proximal and distal ends, the infusion lumen having a distal orifice at the distal end, wherein the flexible tubular member is configured to infuse the therapy into the target artery through the distal orifice;

ii) an expandable occluder mounted at the distal end of the tubular member; and iii) a pressure sensor to sense fluid pressure in the target artery distal of the occluder;

b) advancing the occluder of the system to the target artery of the organ;

c) sensing a first pressure in the target artery with the pressure sensor;

d) deploying the occluder within the target artery to at least partially reduce the fluid pressure within the target artery distal of the occluder;

e) sensing, with the pressure sensor, a stabilized pressure in the target artery after deploying the occluder;

f) then infusing the therapy through the infusion lumen and out of the distal orifice at a constant rate and a variable infusion pressure higher than the stabilized pressure, the variable infusion pressure having a peak pressure sensed by the pressure sensor;

g) upon sensing, with the pressure sensor, a decrease in the variable infusion pressure from the peak pressure by at least 3%, stopping the infusing;

h) waiting for the stabilized pressure in the target artery to return to a lower pressure determined for re-infusion; and i) repeating steps f) through h) until the dose of the therapy has been delivered to the patient.

9. The method of claim 8, wherein infusing is stopped when the decrease in variable infusion pressure from the peak pressure is by at least 5%.

10. The method of claim 8, wherein at least one of the stabilized pressure, the variable infusion pressure, the peak pressure, and the lower pressure is an average lower pressure over time.

11. The method of claim 8, wherein the stabilized pressure in the target artery is an average stabilized pressure over time, the variable infusion pressure is an average running variable infusion pressure over time, the peak pressure is an average peak pressure over time, and the lower pressure is an average lower pressure over time.

12. A method of delivering a dose of a therapy through a target artery to a solid tissue of a patient, comprising:

a) providing a pressure directed therapy system for delivering the therapy to the target artery feeding the solid tissue of the patient, the system having, i) a flexible tubular member having a proximal end and a distal end, an infusion lumen extending between the proximal and distal ends, the infusion lumen having a distal orifice at the distal end, wherein the flexible tubular member is configured to infuse the therapy into the target artery through the distal orifice;

ii) an expandable occluder mounted at the distal end of the tubular member, the occluder having a reduced diameter first configuration for advancement through the target artery and an expanded second configuration for occluding flow of blood within the target artery, the occluder having an impermeable coating on a portion thereof that prevents passage of blood through the impermeable coating; and iii) a pressure sensor to sense fluid pressure in the target artery distal of the occluder;

b) advancing a portion of the pressure directed therapy system into the target artery while the occluder is in the first configuration;

c) using the pressure sensor to determine a baseline pressure in the target artery; then, d) expanding the occluder into the second configuration to effect reduction of the pressure in the target artery by at least 20 percent below the baseline pressure to a second pressure, wherein the second pressure primes the target artery for uptake of the therapy; and then, e) infusing the therapy into the target artery at an infusion pressure exceeding the baseline pressure.

13. The method of claim 12, wherein:

the pressure in the target artery is reduced by at least 40 percent below the baseline pressure prior to infusing the therapy.

14. The method of claim 12, wherein:

the pressure in the target artery is reduced by at least 50 percent below the baseline pressure prior to infusing the therapy.

15. A method of delivering a dose of a therapy through a target artery to a solid tissue of a patient, comprising:

a) providing a pressure directed therapy system for delivering the therapy to the target artery feeding the solid tissue of the patient, the system comprising, i) a flexible tubular member having a proximal end and a distal end, an infusion lumen extending between the proximal and distal ends, the infusion lumen having a distal orifice at the distal end, wherein the flexible tubular member is configured to infuse the therapy into the target artery through the distal orifice;

ii) an expandable occluder mounted at the distal end of the tubular member, the occluder having a reduced diameter first configuration for advancement through the target artery and an expanded second configuration for occluding flow of blood within the target artery, the occluder having an impermeable coating on a portion thereof that prevents passage of blood through the impermeable coating; and iii) a pressure sensor to sense fluid pressure in the target artery distal of the occluder;

b) advancing a portion of the pressure directed therapy system into the target artery while the occluder is in the first configuration;

c) using the pressure sensor to determine a baseline pressure in the target artery; then, d) expanding the occluder into the second configuration to effect reduction of the pressure in the target artery below the baseline pressure to a second pressure, wherein the second pressure primes the target artery for uptake of the therapy; and then, e) infusing the therapy into the target artery at an infusion pressure exceeding the baseline pressure;

f) tracking a running peak infusion pressure;

g) upon sensing, with the pressure sensor, a predetermined decrease in the infusion pressure relative to the tracked running peak infusion pressure, stopping infusion;

h) waiting for the pressure in the target artery to return to the within ±10% of the baseline pressure; and then i) repeating steps f) through h) until the dose of the therapy has been delivered to the patient.

\* \* \* \* \*